United States Patent
Nakashima et al.

(10) Patent No.: US 6,922,577 B2
(45) Date of Patent: Jul. 26, 2005

(54) OPTICAL MEASURING DEVICE HAVING D.C. COMPONENT ELIMINATION

(75) Inventors: Tetsuya Nakashima, Ichinomiya (JP); Yasuji Inobe, Nagoya (JP); Seiji Nagakusa, Kasugai (JP); Teiyuu Kimura, Nagoya (JP)

(73) Assignee: Denso Corporation, Kariya (JP)

( * ) Notice: Subject to any disclaimer, the term of this patent is extended or adjusted under 35 U.S.C. 154(b) by 83 days.

(21) Appl. No.: 10/360,704

(22) Filed: Feb. 10, 2003

(65) Prior Publication Data

US 2003/0158486 A1 Aug. 21, 2003

(30) Foreign Application Priority Data

Feb. 15, 2002 (JP) ........................................ 2002-038434

(51) Int. Cl.[7] .............................. A61B 5/00; A61B 5/02
(52) U.S. Cl. ..................... 600/330; 600/310; 600/500; 600/479
(58) Field of Search ..................... 600/310, 473–477, 600/479–481, 500, 504, 507, 330

(56) References Cited

U.S. PATENT DOCUMENTS

| | | | | |
|---|---|---|---|---|
| 4,198,988 A | * | 4/1980 | Lovelace et al. | 600/479 |
| 4,800,495 A | * | 1/1989 | Smith | 600/322 |
| 4,802,486 A | * | 2/1989 | Goodman et al. | 600/324 |
| 4,824,242 A | * | 4/1989 | Frick et al. | 356/41 |
| 5,078,136 A | * | 1/1992 | Stone et al. | 600/310 |
| 5,351,685 A | * | 10/1994 | Potratz | 600/330 |
| 5,522,388 A | | 6/1996 | Ishikawa et al. | |
| 5,632,272 A | * | 5/1997 | Diab et al. | 600/323 |
| 6,553,242 B1 | * | 4/2003 | Sarussi | 600/330 |

FOREIGN PATENT DOCUMENTS

JP    A-9-24028    1/1997

* cited by examiner

Primary Examiner—Eric F. Winakur
Assistant Examiner—Navin Natnithithadha
(74) Attorney, Agent, or Firm—Posz Law Group, PLC

(57) ABSTRACT

An optical measuring device includes a sensor which emits light flashes toward a subject of detection with a light emitting element which is supplied with electric power from a rechargeable battery for a certain duration at certain intervals and receives reflected light from the subject with a light sensitive element. A subtractor subtracts a d.c. component from a sensed signal provided by the light sensitive element, thereby extracting a variation component. The subtractor has its output signal amplified with an amplifier, with the output thereof being A/D-converted with an A/D converter.

11 Claims, 9 Drawing Sheets

OPTICAL MEASURING DEVICE HAVING D.C. COMPONENT ELIMINATION

CROSS REFERENCE TO RELATED APPLICATION

This application is based on and incorporates herein by reference Japanese Patent Application No. 2002-38434 filed on Feb. 15, 2002.

FIELD OF THE INVENTION

The present invention relates to an optical measuring device which can be applied to, for example, an device which is put on a part of a human body to sense the blood flow, etc. in the form of electrical signal for the diagnostic measurement.

BACKGROUND OF THE INVENTION

Various portable optical measuring devices for sensing a bioactive signal are proposed. This device is used by being put on the arm, etc. of a subject person. It comprises a sensor which detects a bioactive signal, a signal transmission circuit which sends the signal detected by the sensor to a monitoring unit, and a battery which supplies power to the sensor and the signal transmission circuit.

When it is intended to monitor health condition of a subject person accurately, frequent detection of bioactive signal is required, which results in an increased power consumption of the device. For the optical measuring device which is put on the arm, etc. of a subject person, it is not suitable to incorporate a large battery of large power capacity. On this account, the user is required to replace the battery frequently, resulting in a troublesome operation and higher running cost.

Primary data produced by the device from the bioactive signal are data related to time, such as the number of heart beats and the intervals of heart beats. It is difficult to get data necessary for the prediction of abnormality of body, e.g., data of the absolute value of the heart beat amplitude (absolute value of the optically sensed signal) and data of the time-wise variation and small variation of the amplitude on the time axis.

To reduce the power consumption, it is proposed to construct an optical measuring device as shown in FIG. 13. This device includes a light emitting element 201 and a light sensitive element 202, which is a.c.-coupled through a capacitor 203 to an amplifier 204. The output signal of the amplifier 204 is processed by an A/D converter 205. For the output signal V1 of the light sensitive element 202, the amplifier 204 has its input signal V2 alternating across a zero d.c. voltage level and produces an amplified signal V3, as shown in FIG. 14.

It is also proposed, as shown in FIG. 15, to activate a light emitting element 301 is in a certain duty cycle so that it consumes less power for light emission. Specifically, the current supply to the light emitting element 301 is turned on and off, with the output thereof being amplified with an amplifier 303 and thereafter A/D-converted by an A/D converter 304. In this case, however, the amplifier 303 must cover in its full-scale input range Vf a ripple component which floats from zero volt as shown in FIG. 16, and a resulting small amplitude of ripple component relative to the full scale range Vf results in a poor accuracy of A/D conversion output. Namely, a small sensed signal having a large d.c. component easily exceeds the full-scale range Vf when it is amplified intact.

SUMMARY OF THE INVENTION

The present invention has been contemplated under such circumstances, and its object is to provide an optical measuring device which is accurate in sensing a bioactive signal while reducing the power consumption.

According to the present invention, an optical measuring device comprises a sensor which emits light flashes to a subject of detection periodically and receives reflected light from the subject, a subtractor which subtracts a d.c. component from the sensed signal thereby extracting a variation component, an amplifier which amplifies the output signal of the subtractor, and an A/D converter which implements the A/D conversion for the output signal of the amplifier. As the amplitude of the amplifier output is large, the larger signal amplitude allows a shorter duration of light emission of the sensor in the duty cycle at the sampling intervals.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

An embodiment of this invention will be explained with reference to the drawings.

Figure 1:
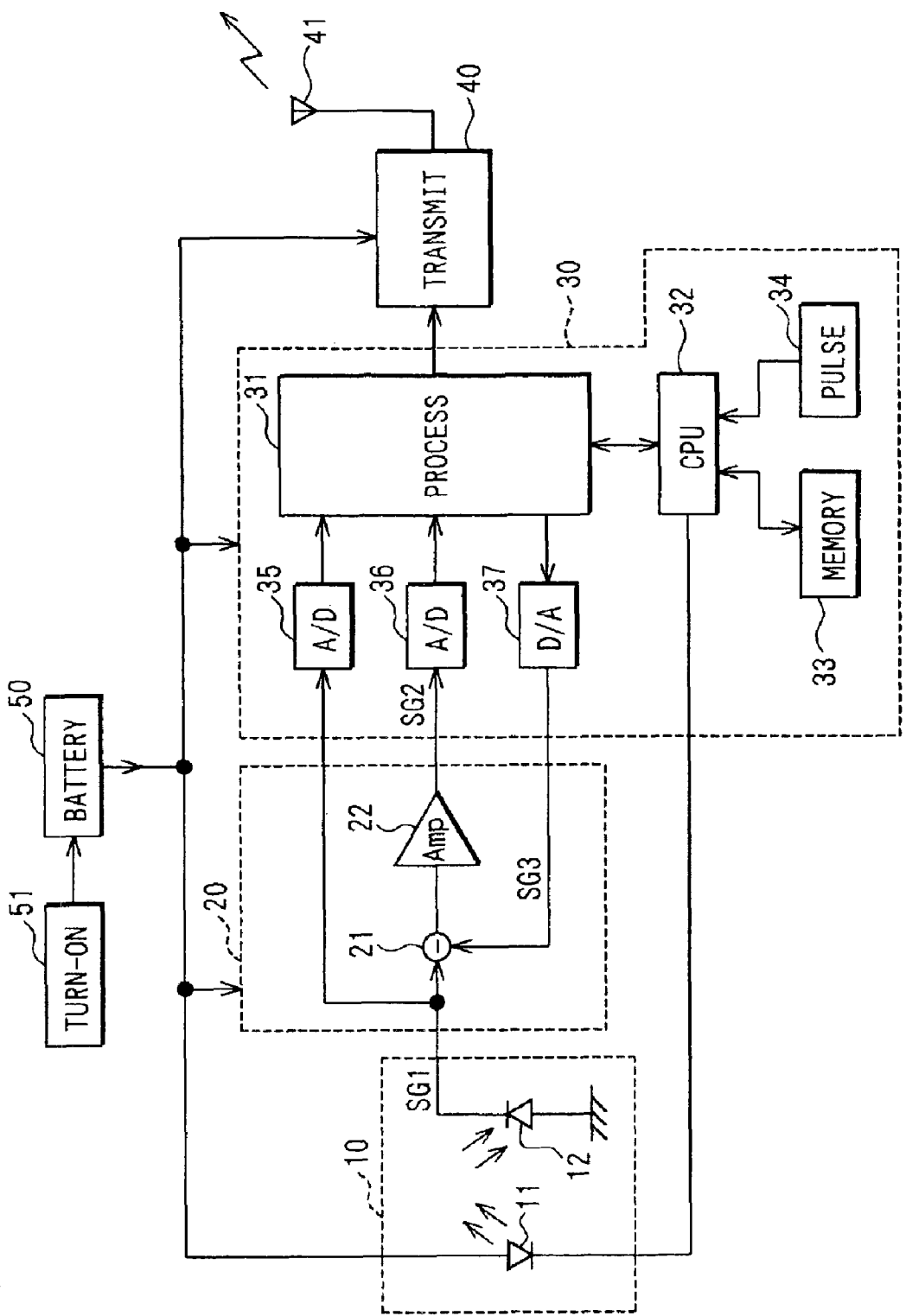
FIG. 1 is a circuit diagram showing an optical measuring device according to an embodiment of this invention.

An optical measuring device of this embodiment is shown in FIG. 1 and designed to sense a bioactive signal. The device is used by being put on a part of a human body, specifically the arm, etc. of a subject person.

The device includes a sensor 10, an analog signal processing circuit 20, a microcomputer 30, a signal transmission circuit 40, an antenna 41, are chargeable battery 50, and a turn-on sensing device 51. The antenna 41 can transmit measured data to a monitoring unit (not shown). The monitoring unit which receives the measured data has a function of battery charger, and it charges the rechargeable battery 50 equipped in the device when the device is placed on it.

The sensor 10 includes a light emitting element 11 and a light sensitive element 12. The light emitting element 11 is a light emitting diode (LED) and the light sensitive element 12 is a photodiode (PD) in this embodiment. The light emitting element 11 emits alight flash to the subject of detection, i.e., blood vessels (skin), and the light sensitive element 12 receives reflected light from the subject. The light emitting element 11 is activated in a predetermined duty cycle to become active for a prescribed duration (80 $\mu$s) at prescribed intervals (50 ms), and the light sensitive element 12 releases a sensed signal SG1 corresponding to the reflected light of emitted light.

The analog signal processing circuit 20 includes a subtractor 21 and an amplifier 22 to implement analog signal processing for the signal SG1 provided by the light sensitive element 12. The subtractor 21 subtracts a d.c. component SG3 from the sensed signal SG1, and the amplifier 22 amplifies the resulting output signal of the subtractor 21.

The microcomputer 30 includes a signal processing circuit 31, a CPU (central processing unit) 32, a memory 33, a pulse generation circuit 34, an A/D converters 35 and 36, and a D/A converter 37. The CPU 32, which controls the operation of the whole microcomputer, activates the light emitting element 11 for the prescribed duration (80 $\mu$s) at the prescribed sampling intervals (50 ms). The A/D converter 36 implements the A/D conversion for the output signal SG2 of the amplifier 22 and applies its output to the signal processing circuit 31. The A/D converter 35 implements the A/D conversion for the sensed signal SG1 from the light sensitive element 12 and applies its output to the signal processing circuit 31. The D/A converter 37 implements the D/A conversion for the output data from the signal processing circuit 31 thereby to produce the signal SG3 having a d.c. level to be fed to the subtractor 21.

The signal processing circuit 31 is connected with the CPU 32. The A/D conversion results provided by the A/D converters 35 and 36 are delivered to the CPU 32 via the signal processing circuit 31, and the CPU 32 returns via the signal processing circuit 31 a value to be D/A-converted by the D/A converter 37. The CPU 32 is connected with the memory 33 and pulse generation circuit 34.

The signal processing circuit 31 is connected with the signal transmission circuit 40, with the antenna 41 being connected thereto. By the operation of the signal transmission circuit 40 and antenna 41, output data resulting from digital processing is sent by being carried on a radio wave to the monitoring unit.

The rechargeable battery 50 stores power for all circuits in the device to operate. The battery power is fed to the sensor 10 (light emitting element 11), analog signal processing circuit 20, microcomputer 30, and signal transmission circuit 40. The light emitting element 11 is supplied with power from the rechargeable battery 50 for the prescribed duration (80 $\mu$s) at the prescribed sampling intervals (50 ms) to emit light flashes to the subject of detection, i.e., blood vessels (skin).

The rechargeable battery 50 has a signal input from the turn-on sensing device 51. When the user takes the device (optical measuring device) off the monitoring unit (not shown) which has charged the battery, the turn-on sensing device 51 sends a signal to the rechargeable battery 50 to turn on the power supply to all the circuits. The voltage (charged voltage) of the rechargeable battery 50 is monitored by the CPU 32. The CPU 32 is programmed to implement the computational processes shown in FIG. 3 and FIG. 4.

In operation, the pulse generation circuit 34 generates pulses that determine timings of sampling. The CPU 32 responds to the arrival of a sampling time to feed power to the light emitting element 11, and the optical sensing operation commences. The light flash emitted by the light emitting element 11 enters the human body through the skin to reach capillary blood vessels, at which the light is partially absorbed and partially reflected and scattered. The reflected light comes out of the body, and is received by the light sensitive element 12.

The reflected light received by the light sensitive element 12 includes a component which is reflected by such an internal body part as capillary blood vessels and a component which is reflected by the skin surface. Accordingly, the output signal SG1 of the light sensitive element 12 includes a ripple component (variation component) super imposed on a d.c. component which is attributable to the reflected light component of skin surface reflection, as shown by the waveform SG1 of FIG. 2.

The sensed signal SG1 is applied to the analog signal processing circuit 20, in which the subtractor 21 subtracts the d.c. component SG3 from the sensed signal SG1 to extract a ripple component (variation component). At the extraction of ripple component of the immediate sampling time, the CPU 32 adjusts the d.c. component level to be given to the subtractor 21. It feeds d.c. component data, which is estimated based on the variation of d.c. component in the past, back to the D/A converter 37. Namely, the CPU (central processing unit) 32 computes a d.c. component and feeds the result back to the analog signal processing circuit 20.

Specifically, the CPU 32 implements: (i) an anticipation process in case when the d.c. component varies gradually, and (ii) a process for minimizing the dropout of data by feeding back the latest d.c. component value immediately when the d.c. component has varied abruptly due to the motion of subject body or the movement of sensor. These processes (i) and (ii) will be explained specifically later with reference to FIG. 3 and FIG. 4.

The ripple component of the signal SG1 from the light sensitive element 12 is very small, and therefore the output of the subtractor 21 is amplified by the amplifier 22 in the analog signal processing circuit 20 and then A/D-converted by the A/D converter 36. At the same time, the output signal SG1 of the light sensitive element 12 is A/D-converted directly by the A/D converter 35. Both digital data released by the A/D converters 35 and 36 are applied to the CPU 32 via the signal processing circuit 31.

The data provided by the A/D converter 36 (ripple component plus d.c. component) and the data provided by the A/D converter 35 are stored in the memory 33. After the data have been stored, the CPU 32 cuts off the power supply to the light emitting element (LED) 11 of the sensor 10. Subsequently, the data transmission operation takes place.

This series of operations is carried out specifically as follows.

Figure 3:
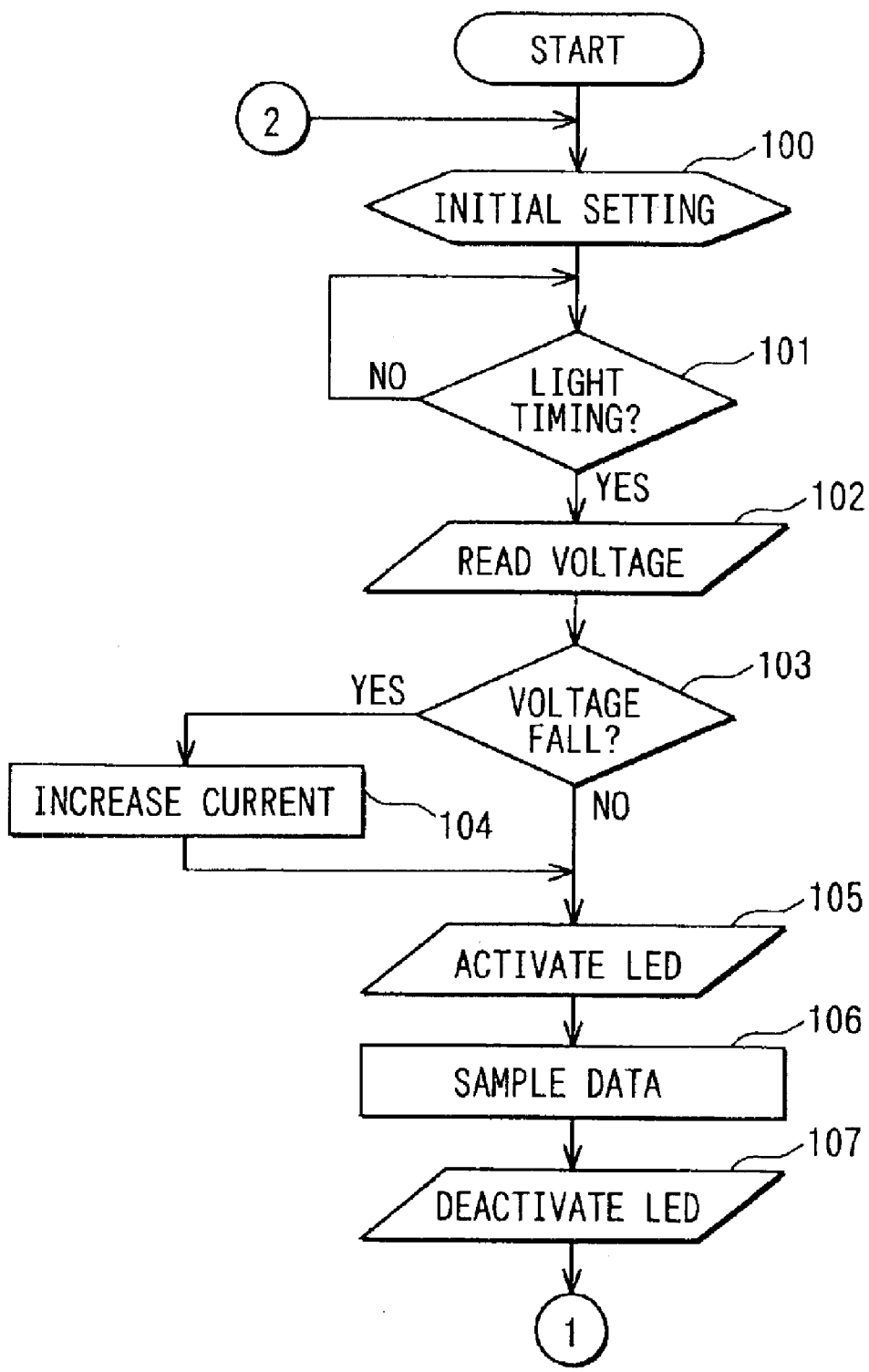
FIG. 3 and FIG. 4 are flowcharts used to explain the operation of the device shown in FIG. 1.

The CPU 32 implements the initial setting in Step 100 in FIG. 3. Specifically, it clears the variables and establishes the nominal sampling timing data (20 Hz), the communication baud rate and the communication format. The CPU 32 waits the light emission timing in step 101. At the arrival of light emission timing, the CPU 32 reads the voltage of the rechargeable battery 50 in Step 102, and detects the event of voltage fall in Step 103. Upon detecting a voltage fall, the CPU 32 corrects the supply current to the light emitting element 11 thereby to maintain the normal light emission output in Step 104.

Subsequently, the CPU 32 activates the light emitting element 11 to light in Step 105. In Step 106, the CPU 32 samples A/D-converted data of the signal SG1 which is produced by the light sensitive element 12 and A/D-converted data of the signal SG2 which is derived from SG1 and processed by the subtractor 21 and amplifier 22. The CPU 32 deactivates the light emitting element 11 in Step 107.

The CPU 32 checks at Steps 108 and 109 whether or not the data value of signal SG1 is outside the range of a prescribed upper limit UL and lower limit LL. Upon confirming the data value within the range, the CPU 32 stores the data in the memory 33 in Step 110. If the data value is found to be beyond the upper or lower limit, the CPU 32 modifies the d.c. component level to be subtracted in Step 111. Specifically, if the data value of signal SG1 is above the upper limit UL, the CPU 32 increases the d.c. component level, or if the data value is below the lower limit LL, the CPU 32 decreases the d.c. component level. By the process of Step 111 and the process of Step 113, the d.c. component level to be subtracted for the next data sampling is modified (anticipatory modification).

Following the operation of Step 110, the CPU 32 checks at Step 112 whether the data value of signal SG2 is rising or falling, and modifies the d.c. component level depending on the rate of rise or fall in Step 113. Specifically, the CPU 32 evaluates the difference between the average value of the latest 32 pieces of data and the average value of the previous 32 pieces of data, multiplies a factor to the difference value, and adds the result to the immediate d.c. component value.

Figure 5:
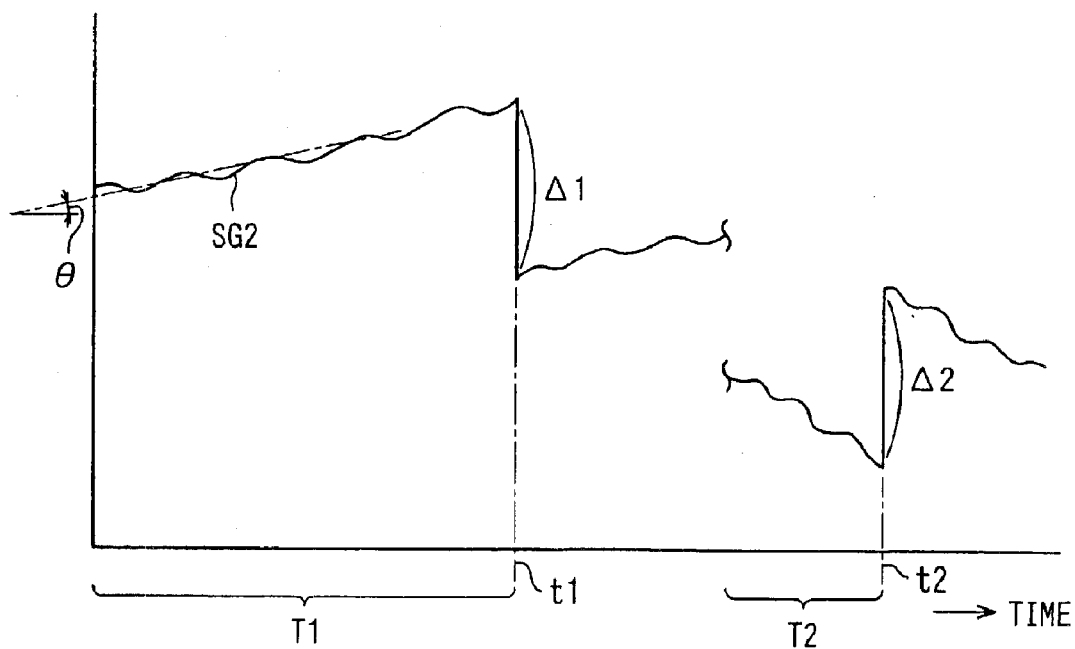
FIG. 5 is a signal diagram used to explain the operation of the device shown in FIG. 1.

More specifically, if the data value increases with time as shown in time span T1 in FIG. 5, the d.c. component level is modified to increase. Due to the rise of the d.c. component level to be subtracted at time point t1, the output of the subtractor 21 in terms of the amplified signal SG2 falls by Δ1. Otherwise, if the data value decreases with time as shown in time span T2 in FIG. 5, the d.c. component level is modified to decrease. Due to the fall of the d.c. component level to be subtracted at time point t2, the output of the subtractor 21 in terms of the amplified signal SG2 rises by Δ2. In this manner, the CPU 32 operates to modify the d.c. component by monitoring the variation of data value provided by the A/D converter 36.

Figure 4:
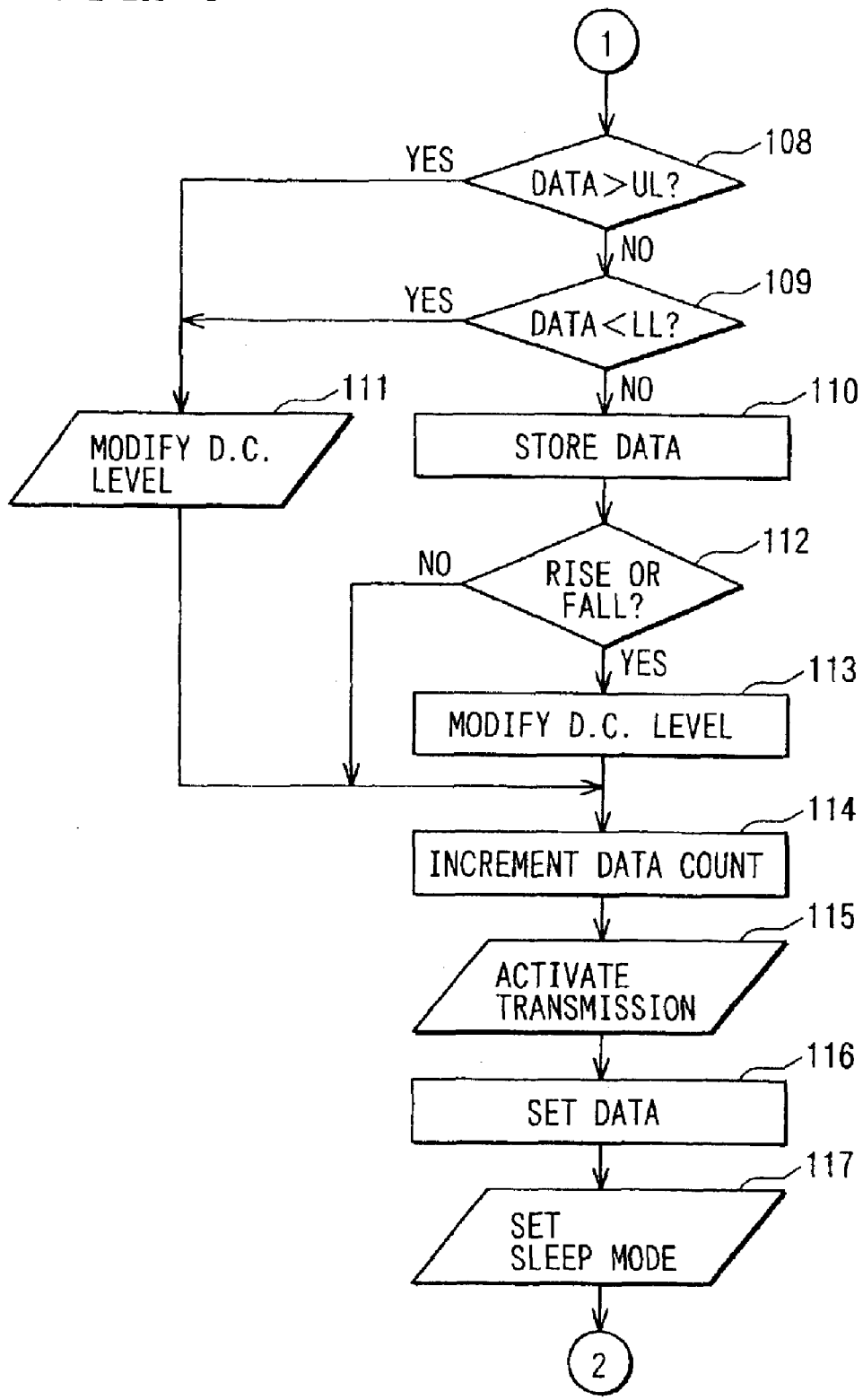

Following the process of Step 111 or Step 113 in FIG. 4, the CPU 32 increments the data counter by 1 in Step 114, and it activates the signal transmission circuit 40 and cancels its sleep mode. The CPU 32 sets transmission data in Step 116, and the data is transmitted by the signal transmission circuit 40 and antenna 41 to the monitoring unit at a prescribed timing. Finally, the CPU 32 deactivates the signal transmission circuit 40 and sets its sleep mode, and returns to Step 100 of FIG. 3.

In regard to the data transmission processes of Steps 114–117 in FIG. 4, data to be transmitted include the ripple component data and d.c. component data which are stored in the memory 33 and the data count value indicative of the sequential number of sampling, and these data are compiled into the communication format. At the commencement of transmission, the signal transmission circuit 40 is switched from the power saving mode (sleep mode) to the transmission mode, and it implements the radio wave transmission to the monitoring unit. On completion of data transmission, the transmission mode is cancelled and the signal transmission circuit 40 is brought to the sleep mode until the next sampling time.

As described above, the d.c. component data in addition to the data of signal SG2 provided by the A/D converter 36 is sent by being carried on a radio wave to the monitoring unit.

When the user places the optical measuring device on the monitoring unit, the built-in charging circuit incorporated in the monitoring unit begins to charge the rechargeable battery 50 in the device. The charging circuit has a full-charge detecting function, by which excessive charging of the battery 50 is avoided even if it is left engaged with the monitoring unit. On the next occasion of use, the optical measuring device starts operating when it is taken off the monitoring unit by the user, and it is operative to sense a bioactive signal by being put on a part of a subject body. The user is not required to replace the battery, and at the same time can reduce the running cost of the device.

In the optical measuring device, much power is consumed for the light emission of the light emitting element 11. A rechargeable battery, which is adopted for the elimination of battery replacement, is in need of load reduction due to its small energy density as compared with a disposable battery. A large proportion of the total power consumed is allotted to the lighting of the light emitting element.

Figure 6:
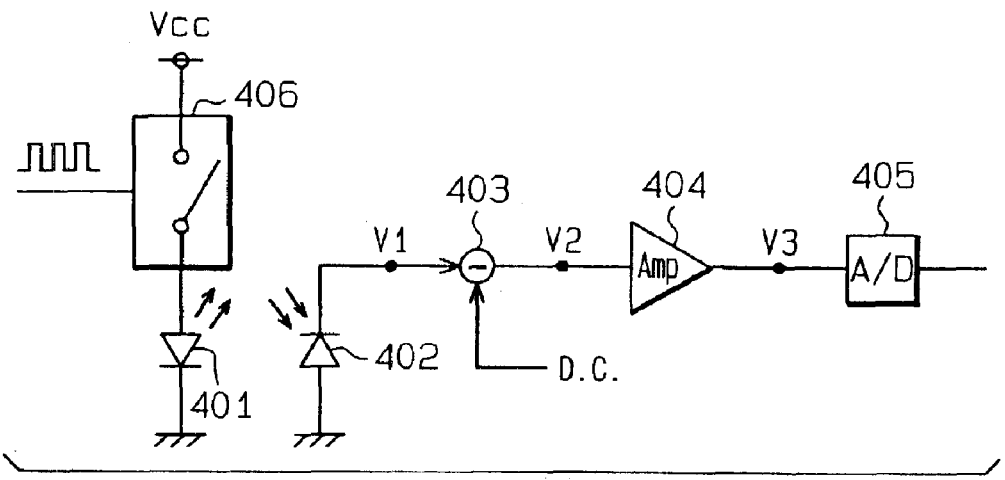
FIG. 6 is a circuit diagram showing an optical measuring device shown in FIG. 1 in a simplified form.
Figure 7:
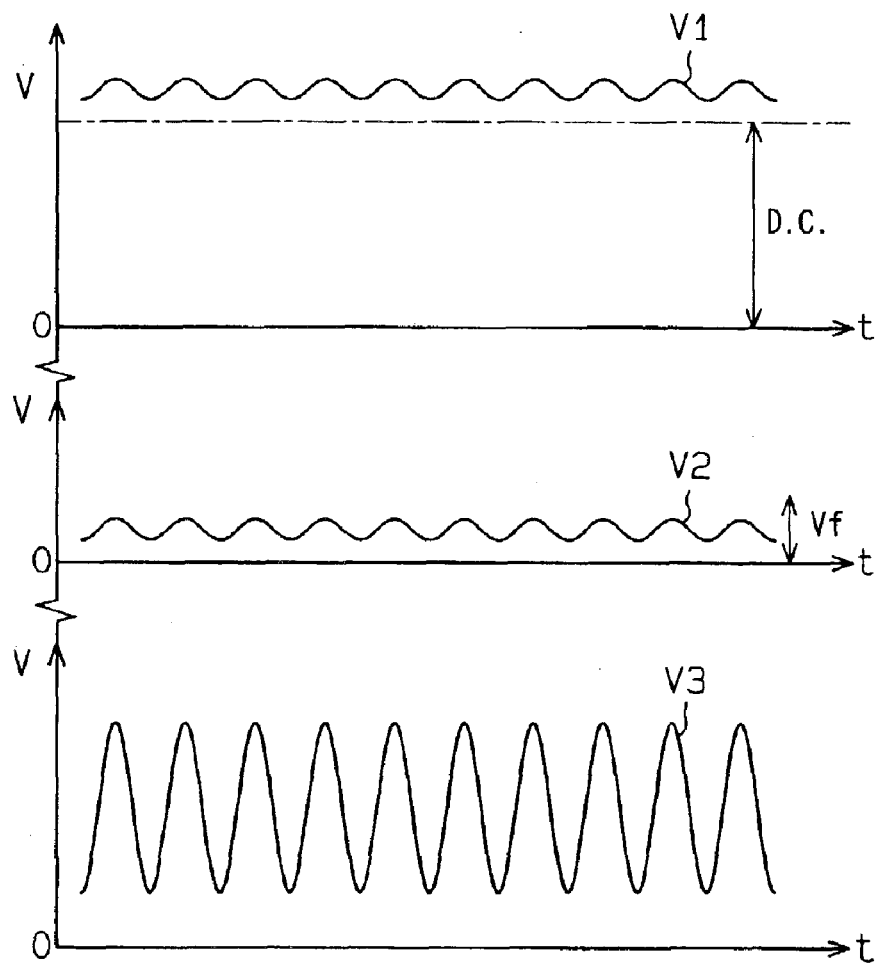
FIG. 7 is a signal diagram used to explain the operation of the device shown in FIG. 6.
Figure 13:
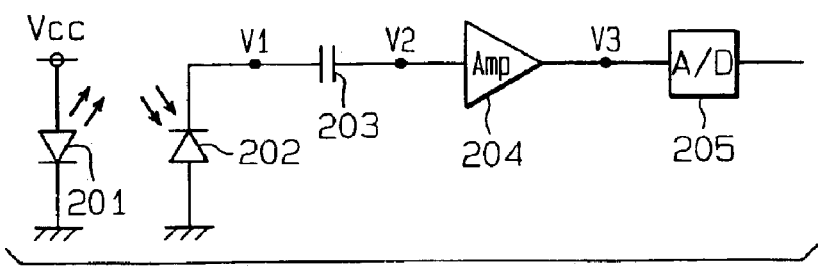
FIG. 13 is a circuit diagram of an optical measuring device according to one related art.
Figure 14:
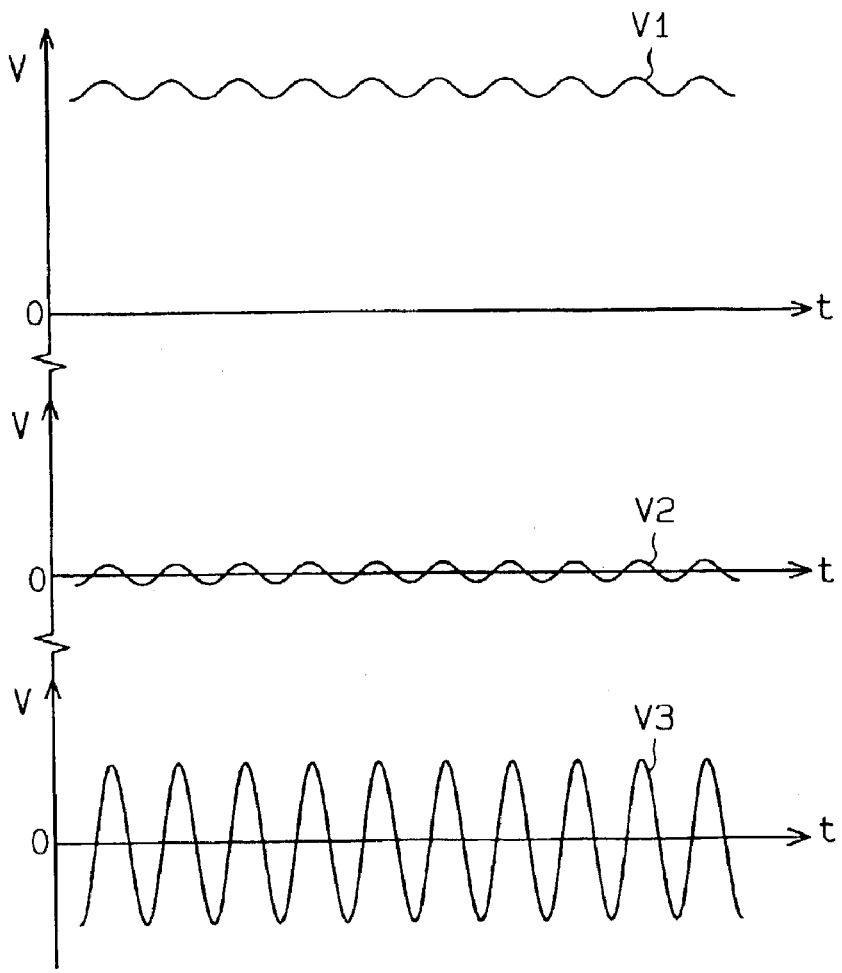
FIG. 14 is a signal diagram used to explain the operation of the device shown in FIG. 13.
Figure 15:
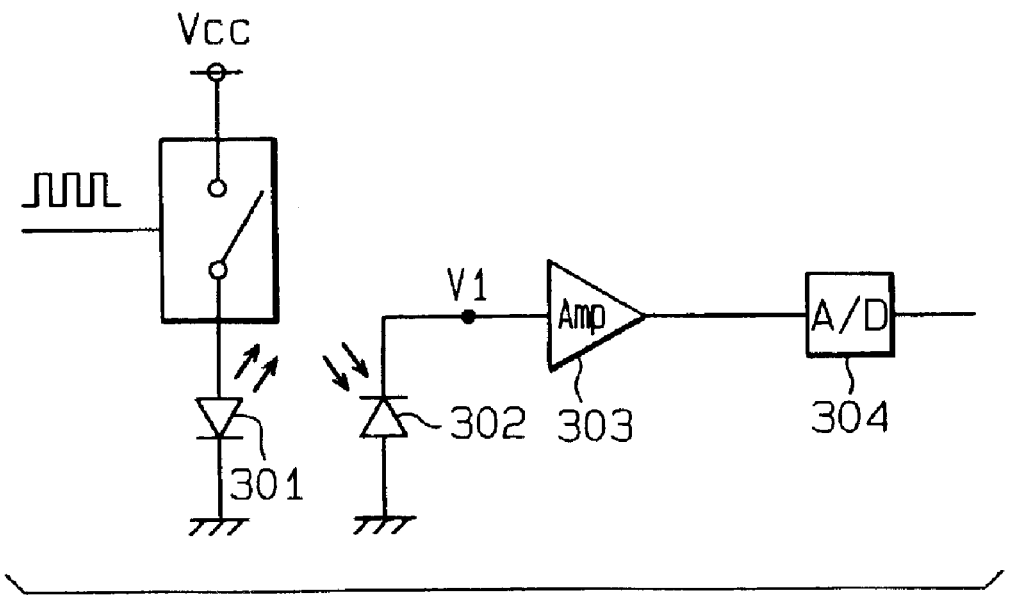
FIG. 15 is a circuit diagram of an optical measuring device according to another related art.
Figure 16:
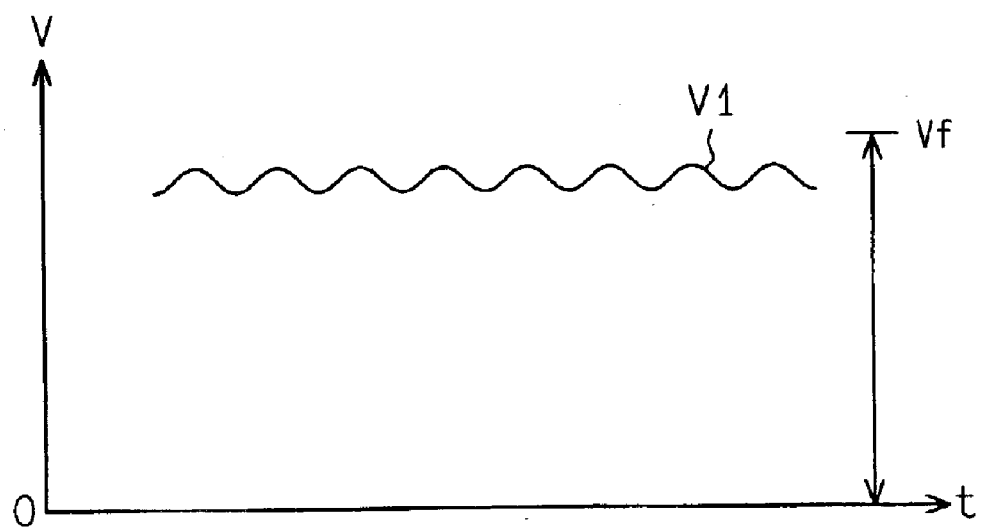
FIG. 16 is a signal diagram used to explain the operation of the device shown in FIG. 15.

The principle of the above embodiment is shown in FIG. 6 in a simplified manner in comparison with the related art device shown in FIG. 13 and FIG. 15. In this simplified arrangement, a light emitting element 401 is activated periodically by turning on and off a switch 405. The sensed signal V1 of a light sensitive element 402 is applied to a subtractor 403, by which the d.c. component is subtracted from the signal V1, and the resulting signal V2 is amplified with an amplifier 404. The amplified signal V3 is applied to an A/D converter. As a result, as shown in FIG. 7, the signal V2 resulting from the subtraction of the d.c. component from the sensed signal V1 is amplified by the amplifier 404. This amplified signal V3 is large in amplitude in the full-scale range, and accordingly provides an accurate A/D conversion result.

Figure 8:
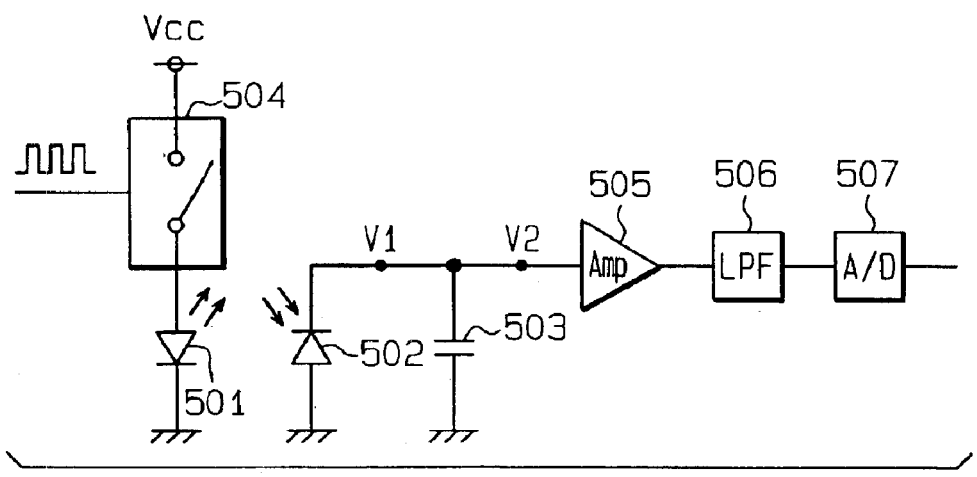
FIG. 8 is a circuit diagram of an optical measuring device according to a comparative arrangement used in comparison with the device shown in FIG. 6.

Here, a different circuit arrangement of an optical measuring device is shown in FIG. 8 for comparison with the device shown in FIG. 6. This device includes a light emitting element 501, a light sensitive element 502 and a capacitor 503, with the coupling capacitor (capacitor 503) allowing the passage of only a small variation component, while blocking a d.c. component. An amplifier 505, a low pass filter 506 and an A/D converter 507 are connected to the capacitor 503.

Figure 9:
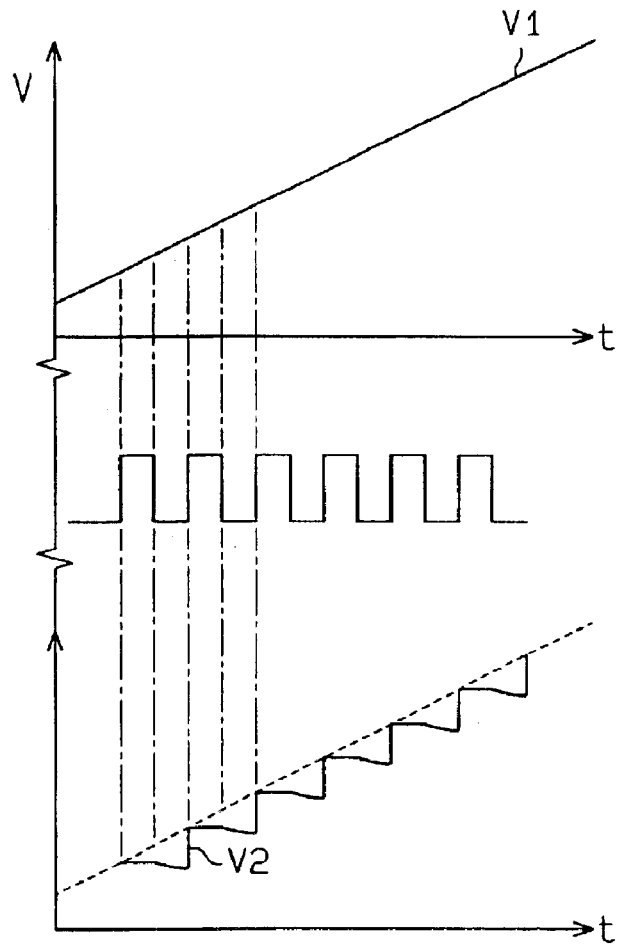
FIG. 9 is a signal diagram used to explain the operation of the device shown in FIG. 8.
Figure 10:
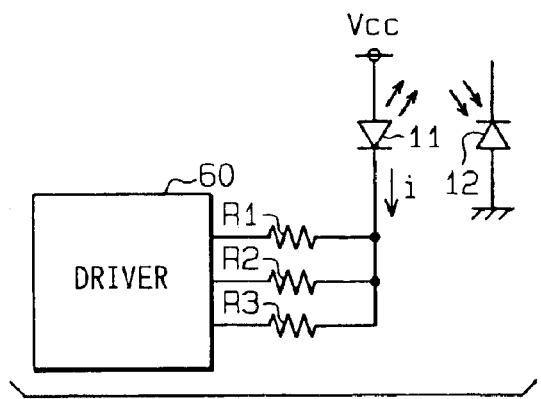
FIG. 10 is a circuit diagram used to drive a sensor of the device shown in FIG. 1.

For the reduction of power consumption, a switch 504 is turned on for a short time (duration of light emission of the light emitting element 501). However, if the proportion of discharge time which is determined from the time constant associated with the capacitor 503 is large, a voltage enough to retain a required signal accuracy cannot be held, and therefore the duration of light emission (duty ratio) cannot be reduced. Namely, for dealing with a bioactive signal which is a continuous analog signal, the light emitting element 501 needs to be activated for a certain duration. Moreover, a quasi rippling signal V2 which is formed by the capacitor 503 from a rippling signal V1, which is shown to be linear in FIG. 9 has a lowered accuracy. Accordingly, the power consumption and the signal accuracy are in a "trade off" relation in the circuit arrangement shown in FIG. 8. Consequently the on-time of duty cycle is determined to be around 20% from the viewpoint of allowable score of accuracy.

In contrast, the device shown in FIG. 1 can process the data of sensed rippling signal intact and therefore can reduce the on-time of duty cycle to the sole time length necessary for sensing (signal propagation time of analog circuit parts plus A/D conversion time of microcomputer, which totally equal 80 $\mu$s). The duty ratio of light emission is 80 ($\mu$s) divided by a sampling period of 50 (ms), which equals 0.16%, and the power consumption of the sensor can be reduced from 20% of the case of arrangement of FIG. 8 to 0.16%, i.e., reduced to 1/100 or less.

After the bioactive signal data has been stored in the memory 33, the light emitting element 11 of the sensor is turned off until next sampling time, i.e., the light emitting element is kept off in 99.8% of sampling cycle, so that the power consumption is reduced. In consequence, the reduction of power consumption can be accomplished regardless of the signal accuracy.

In the arrangement of FIG. 8, in which a d.c. component is blocked by means of a coupling capacitor (capacitor 503) while conducting only a small variation component, data of a very low frequency component (swell of the major line of rippling signal) which carries abnormality-indicative information of the subject, etc. and data of a signal absolute value are lost.

In contrast, this embodiment of invention is designed to fetch indirectly a d.c. component (SG3) included in the rippling signal via the A/D converter 36, process it with the microcomputer 30, and feed the result back to the subtractor 21, thereby accomplishing the collection of both the ripple data and d.c. component data. Namely, addition of the ripple data to the d.c. component data provides the crude data, enabling the collection of absolute signal value. Specifically, only a small signal resulting from the subtraction by the subtractor 21 of the analog signal processing circuit 20 is amplified and stored as bioactive signal data in the memory 33. At the same time, the d.c. component data which has been fed back to the analog signal processing circuit 20 is also stored in the memory 33, and these total data represent the absolute value of bioactive signal, enabling the detection of a small amplitude variation. Inconsequence, it becomes possible to measure the swell (swing) of the major line of rippling signal as shown in FIG. 2.

Moreover, in the arrangement of FIG. 8, the rippling signal is amplified with the amplifier 505 so as to raise the resolution of data, and thereafter the quasi waveform produced with the capacitor 503 is made close to the ripple waveform by conducting it through a low-pass filter 506 (for smoothing the stepped waveform), and resulting data released by the A/D converter 507 is collected. Therefore, the signal accuracy lowers at the occurrence of a sharp variation.

In contrast, the device of the embodiment (FIG. 1 and FIG. 6) deals with the crude data, enabling the microcomputer 30 to fetch data immediately after signal amplification, and accurate data collection can be accomplished.

Figure 2:
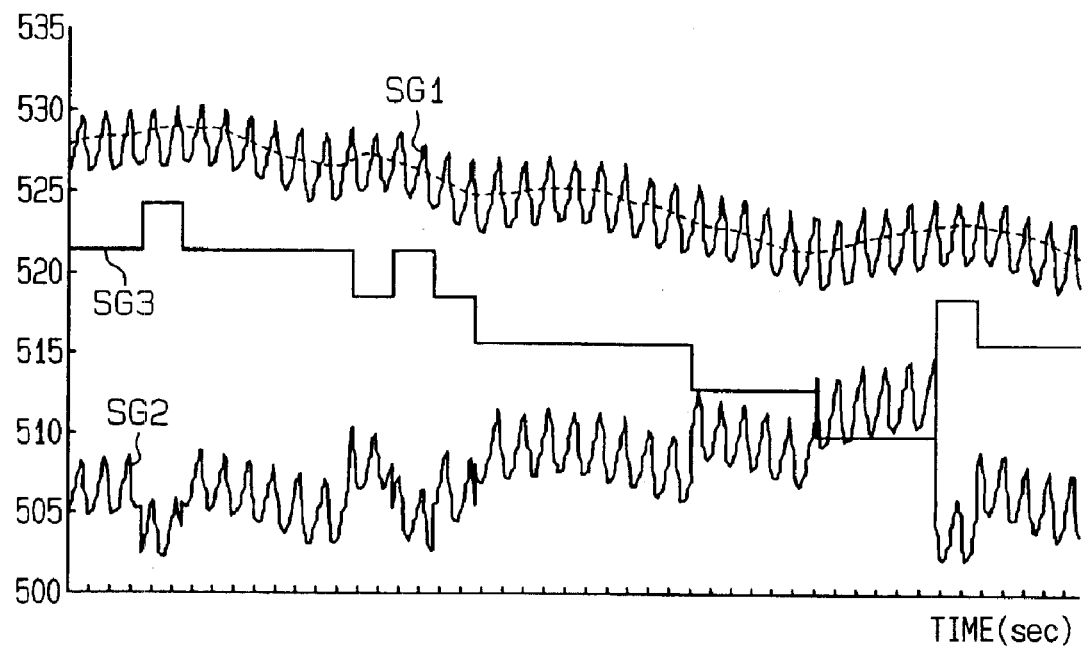
FIG. 2 is a signal used to explain the operation of the device shown in FIG. 1.

On the flowcharts (algorithm of feedback data processing) shown in FIG. 3 and FIG. 4, missing of data at the occurrence of a sharp variation of rippling signal due to the body motion or sensor movement and at the swing out of signal beyond the input range due to the swelling of the major line of rippling signal shown in FIG. 2 can be minimized. Namely, a sharp variation of rippling signal can be dealt by the implementation of Steps 108,109 and 111 of FIG. 4, and a trend of signal rise or fall can be anticipated by the implementation of steps 112 and 113. Inconsequence, more accurate measurement is made possible.

Figure 12:
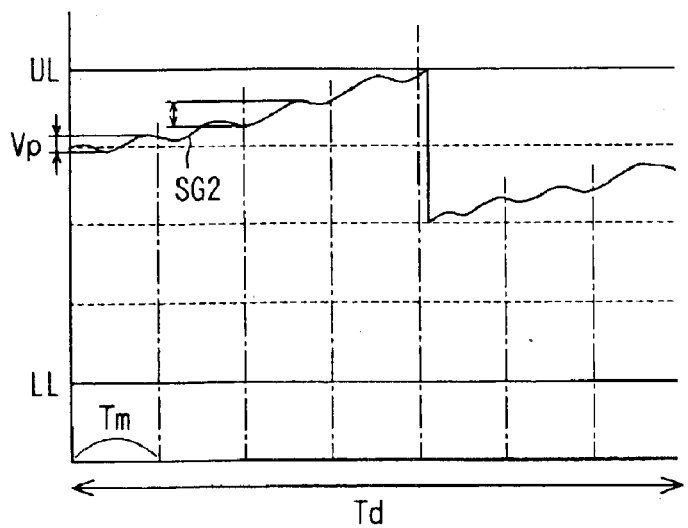

The arrangement of FIG. 12 collects only ripple data (variation value), and processes the collected data to get information on the intervals (frequency) of rippling signal. The device of this embodiment can collect d.c. component data in addition to ripple data (variation value), and it becomes possible to collect other information such as the swelling of rippling signal major line shown in FIG. 2 and the absolute value of amplitude (absolute value of the sensed signal).

As described above, the optical measuring device of this embodiment is capable of reducing the power consumption without sacrificing the accuracy of sensing of the bioactive signal which includes a small amplitude variation. The device provides a larger amplified signal amplitude as compared with the scheme shown in FIG. 15, enabling the reduction of the duration of lighting of the light emitting element 11 which is activated in a duty cycle at sampling intervals. The device is accurate in detection and yet is capable of reducing the power consumption.

The sensor 10 of the optical measuring device shown in FIG. 1, particularly the light emitting element 11 is activated by a driver 60 having resistors R1, R2 and R3, by means of which the drive current of the element 11 is made variable. One of the resistors R1-R3 is selected to set the light output of the element 11 in response to at least the value of data provided by the A/D converter 36 in FIG. 1.

Figure 11:
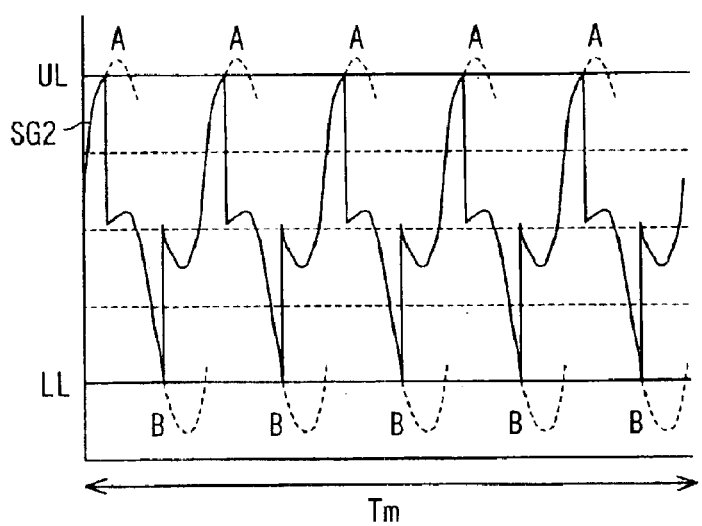
FIG. 11 and FIG. 12 are signal diagrams used to explain the operation of the device shown in FIG. 1.

Specifically, the value of data provided by the A/D converter 36 is limited to the upper limit level UL and the lower limit level LL as shown in FIG. 11, and the d.c. component level is raised by a prescribed amount if the sensed signal level SG2 reaches the upper limit level UL as indicated as phenomenon A, or the d.c. component level is lowered by the prescribed amount if the sensed signal level SG2 reaches the lower limit level LL as indicated as phenomenon B. The number of events of level shift (number of occurrences of phenomenon A and phenomenon B) is counted in a prescribed time span of measurement Tm, and the drive current i of the light emitting element 11 is decreased (light output is reduced) if the count value exceeds a prescribed number. In this manner, the sensitivity of device can be lowered when the amplitude of ripple is large (i.e., automatic adjustment of sensitivity). Alternatively, the light output of the light emitting element 11 may be reduced when the value of data provided by the A/D converter 36 is out of a prescribed range continuously.

The peak-to-peak value (amplitude) Vp of the signal SG2 is evaluated as shown in FIG. 12, and the drive current i of the light emitting element 11 is increased (light output is raised), if the number of ripple cycles in which the value of Vp is within a prescribed value in a prescribed time span of determination Td exceeds a prescribed number. In this manner, the sensitivity of device can be raised when the amplitude of ripple is small (i.e., automatic adjustment of sensitivity). Alternatively, the light output of the light emitting element 11 may be raised when the value of data provided by the A/D converter 36 is within a prescribed range.

The present invention should not be limited to the above embodiment, but may be implemented in various other ways without departing from the spirit of the invention.

What is claimed is:

1. An optical measuring device, comprising:
   a sensor having a light emitting element which emits light flashes to a subject of detection by being supplied with electric power from a battery for a prescribed duration at prescribed intervals and a light sensitive element which receives reflected light from the subject;
   a subtractor which subtracts a d.c. component from a sensed signal provided by the light sensitive element, thereby extracting a variation component;
   an amplifier which amplifies an output signal of the subtractor;
   an A/D converter which implements an A/D conversion for an output signal of the amplifier; and
   a d.c. component modifying means which modifies a d.c. component level based on an A/D-converted value of the sensed signal provided by the light sensitive element.

2. An optical measuring device according to claim 1, wherein the d.c. component modifying means raises the d.c. component level when the ND-converted value of the sensed signal provided by the light sensitive element becomes larger than a prescribed upper limit value, and lowers the d.c. component level when the A/D-converted value of the sensed signal provided by the light sensitive element becomes smaller than a prescribed lower limit value.

3. An optical measuring device according to claim 1, wherein the sensor is used by being put on a part of a human body, with the light emitting element being adapted to emit the light flashes toward a blood vessel as a subject of detection.

4. An optical measuring device, comprising:
   a sensor having a light emitting element which emits light flashes to a subject of detection by being supplied with electric power from a battery for a prescribed duration at prescribed intervals and a light sensitive element which receives reflected light from the subject;
   a subtractor which subtracts a d.c. component from a sensed signal provided by the light sensitive element, thereby extracting a variation component;
   an amplifier which amplifies an output signal of the subtractor;
   an A/D converter which implements an A/D conversion for an output signal of the amplifier;
   wherein data of the d.c. component of the sensed signal is delivered in addition to a data of A/D-converted value provided by the A/D converter, and
   wherein the data of the d.c. component of the sensed signal is determined from the sensed signal without being applied to the subtractor.

5. An optical measuring device according to claim 4, wherein the sensor is used by being put on a part of a human body, with the light emitting element being adapted to emit the light flashes toward a blood vessel as a subject of detection.

6. An optical measuring device comprising:
   a sensor having a light emitting element which emits light flashes to a subject of detection by being supplied with electric power from a battery for a prescribed duration at prescribed intervals and a light sensitive element which receives reflected light from the subject;
   a subtractor which subtracts a d.c. component from a sensed signal provided by the light sensitive element, thereby extracting a variation component;
   an amplifier which amplifies an output signal of the subtractor;
   an A/D converter which implements an A/D conversion for an output signal of the amplifier; and
   control means for decreasing a level of the d.c. component by a prescribed amount each time an A/D-converted value provided by the A/D converter exceeds a prescribed upper level, and for decreasing the electric power supplied to the light emitting element when the level decreasing control means continues to decrease the level of the d.c. component a predetermined number of times.

7. An optical measuring device according to claim 6, wherein the sensor is used by being put on a part of a human body, with the light emitting element being adapted to emit the light flashes toward a blood vessel as a subject of detection.

8. An optical measuring device according to claim 6, wherein the sensor is used by being put on a part of a human body, with the light emitting element being adapted to emit the light flashes toward a blood vessel as a subject of detection.

9. An optical measuring device comprising:
   a sensor having a light emitting element which emits light flashes to a subject of detection by being supplied with electric power from a battery for a prescribed duration at prescribed intervals and a light sensitive element which receives reflected light from the subject;
   a subtractor which subtracts a d.c. component from a sensed signal provided by the light sensitive element, thereby extracting a variation component;
   an amplifier which amplifies an output signal of the subtractor;
   an A/D converter which implements an A/D conversion for an output signal of the amplifier; and
   control means for increasing a level of the d.c. component by a prescribed amount each time an A/D-converted value provided by the A/D converter falls below a prescribed lower level, and for decreasing the electric power supplied to the light emitting element when the level increasing control means continues to increase the level of the d.c. component a predetermined number of times.

10. An optical measuring device according to claim 6, wherein the sensor is used by being put on a part of a human body, with the light emitting element being adapted to emit the light flashes toward a blood vessel as a subject of detection.

11. An optical measuring device comprising:
    a sensor having a light emitting element which emits light flashes to a subject of detection by being supplied with electric power from a battery for a prescribed duration at prescribed intervals and a light sensitive element which receives reflected light from the subject;
    a subtractor which subtracts a d.c. component from a sensed signal provided by the light sensitive element, thereby extracting a variation component;
    an amplifier which amplifies an output signal of the subtractor;
    an A/D converter which implements an A/D conversion for an output signal of the amplifier; and
    control means for decreasing a level of the d.c. component by a first prescribed amount each time an A/D-converted value provided by the A/D converter exceeds a prescribed upper level, for increasing the level of the d.c. component by a second prescribed amount each time the A/D-converted value provided by the A/D converter falls below a prescribed lower level, and for decreasing the electric power supplied to the light emitting element when the level of the d.c. component is decreased and increased alternately a predetermined number of times.

* * * * *